United States Patent
Saptharishi et al.

(10) Patent No.: US 7,409,079 B2
(45) Date of Patent: Aug. 5, 2008

(54) CALCIUM SCORING METHOD AND SYSTEM

(75) Inventors: Ramkumar Saptharishi, Bangalore (IN); Heman Malve, Andhra Pradesh (IN); Uday Patil, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 484 days.

(21) Appl. No.: 11/032,412

(22) Filed: Jan. 10, 2005

(65) Prior Publication Data
US 2005/0157917 A1    Jul. 21, 2005

(30) Foreign Application Priority Data
Jan. 20, 2004    (JP)    ............... 2004-011405

(51) Int. Cl.
*G06K 9/00*    (2006.01)
(52) U.S. Cl. .................. 382/131; 382/237; 378/21
(58) Field of Classification Search .......... 382/100, 382/128, 129, 130, 131, 132, 133, 162, 194, 382/199, 219, 224, 232, 260, 274, 276, 291, 382/295, 305, 168, 181, 203, 237, 254; 378/18, 378/8, 21; 514/44; 600/425, 426
See application file for complete search history.

(56) References Cited

U.S. PATENT DOCUMENTS

| | | | |
|---|---|---|---|
| 6,233,304 B1 | 5/2001 | Hu et al. | |
| 6,470,207 B1 * | 10/2002 | Simon et al. | 600/426 |
| 6,560,309 B1 * | 5/2003 | Becker et al. | 378/8 |
| 6,674,834 B1 * | 1/2004 | Acharya et al. | 378/18 |
| 6,697,451 B2 | 2/2004 | Acharya et al. | |
| 7,045,509 B2 * | 5/2006 | Zerhusen | 514/44 |
| 7,130,457 B2 * | 10/2006 | Kaufman et al. | 382/128 |
| 7,142,703 B2 * | 11/2006 | Kaufman et al. | 382/131 |
| 7,194,117 B2 * | 3/2007 | Kaufman et al. | 382/128 |
| 7,209,779 B2 * | 4/2007 | Kaufman et al. | 600/425 |
| 2004/0147838 A1 | 7/2004 | Londt et al. | |

FOREIGN PATENT DOCUMENTS

WO    0055812 A1    9/2000

OTHER PUBLICATIONS

Agatston, Arthur S., M.D., FACC; "Quantification of Coronary Artery Calcium Using Ultrafast Computed Tomogrpahy", JACC vol. 15, No. 4, Mar. 15, 1990:827-832.

Patent Abstracts of Japan, Publication No. 06-261894, published Sep. 20, 1994, Applicant Hitachi Ltd Hitachi Medical Corp, English Abstract.

* cited by examiner

*Primary Examiner*—Seyed Azarian
(74) *Attorney, Agent, or Firm*—Armstrong Teasdale LLP

(57) ABSTRACT

A method of automatically scoring intravascular calcium. The delineation of a body surface is detected in a tomographic image produced by an X-ray CT system. Images of bones are removed from a field encircled with the delineation of the body surface. The delineations of blood vessels are detected in the tomographic image having the bone images removed therefrom. Calcium is scored using the tomographic image having the bone images removed therefrom. Only the scores of intravascular calcium obtained from the fields inside the delineations of the blood vessels are displayed.

18 Claims, 4 Drawing Sheets

FIG. 6
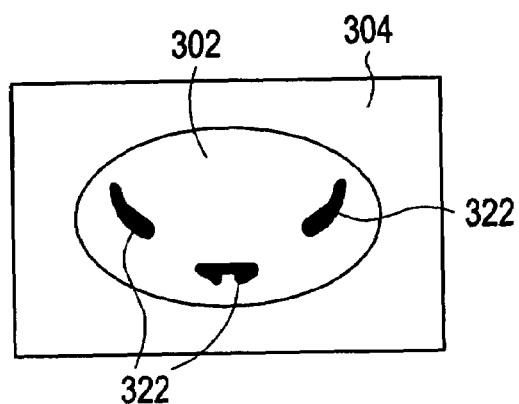
FIG. 7
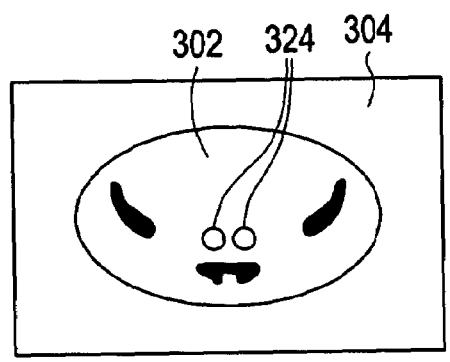
FIG. 8
| RANK | CT NUMBER |
|------|-----------|
| 1 | 130-199 |
| 2 | 200-299 |
| 3 | 300-399 |
| 4 | 400 OR MORE |
FIG. 9
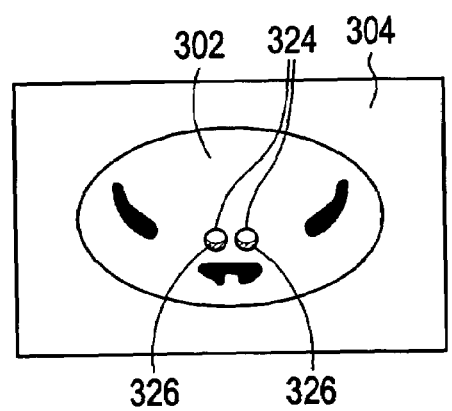

CALCIUM SCORING METHOD AND SYSTEM

CROSS REFERENCE TO RELATED APPLICATIONS

This application claims the benefit of Japanese Application No. 2004-011405 filed Jan. 20, 2004.

BACKGROUND OF THE INVENTION

The present invention relates to a calcium scoring method and system. More particularly, the present invention is concerned with a method and system for scoring calcium using a tomographic image produced by an X-ray CT system.

A tomographic image produced by an X-ray CT system is often used to score calcium. A calcium score is expressed as a product of a rank of a CT number, which is calculated from each pixel value, by the size of a field composed of pixels whose CT numbers rank the same. The calcium scoring is referred to as an Agatston-Janowtiz scoring method (refer to, for example, Non-patent Document 1).

[Non-Patent Document 1] Quantification of Coronary Artery Calcium Using Ultrafast Computed Tomography (Arthur S Agatston et al., JACC, U.S.A., 1990, Vol. 15, 4th Edition, P. 827-P. 832)

Calcium deposited on an intravascular wall obstructs circulation of blood. Scoring such calcium has a clinically significant meaning. However, according to the foregoing method, calcium in every region including bones is scored. A diagnostician has to distinguish blood vessels on the basis of his/her anatomical knowledge and then check calcium scores. This is time-consuming.

SUMMARY OF THE INVENTION

Therefore, an object of the present invention is to provide a method and system for automatically scoring intravascular calcium.

(1) According to one aspect of the present invention for solving the foregoing problem, there is provided a calcium scoring method comprising the steps of: detecting the delineation of a body surface in a tomographic image produced by an X-ray CT system; removing images of bones from a field encircled with the delineation of the body surface; detecting delineations of blood vessels in the tomographic image having the bone images removed therefrom; scoring calcium using the tomographic image having the bone images removed therefrom; and displaying only intravascular calcium scores obtained using the insides of the delineations of the blood vessels.

(2) According to another aspect of the present invention for solving the foregoing object, there is provided a calcium scoring system comprising: a body surface delineation detecting method for detecting the delineation of a body surface in a tomographic image produced by an X-ray CT system; a bone image removing means for removing images of bones from the inside of a field encircled with the delineation of the body surface; a blood vessel delineation detecting means for detecting contours of blood vessels in the tomographic image having the bone images removed therefrom; a scoring means for scoring calcium using the tomographic image having the bone images removed therefrom; and a display means for displaying only intravascular calcium scores obtained using the insides of the delineations of the blood vessels.

Preferably, the delineation of the body surface is detected after a tomographic image is binary-coded, so that the delineation of the body surface can be appropriately detected. Preferably, the bone images are removed after the values of pixels constituting the images of tissues other than the bones are made uniform, so that the bone images can be removed appropriately. Preferably, the delineations of the blood vessels are detected using the Canny edge detector is used, so that the delineations of the blood vessels can be appropriately detected.

Preferably, calcium is scored according to the Agaston and Janowitz scoring method because of high clinical value. Preferably, calcium scores are displayed in the form of color scales, so that the severity of a condition can be discerned.

According to the aspects of the present invention, there is provided a method and system for automatically scoring intravascular calcium. Specifically, the delineation of a body surface in a tomographic image produced by an X-ray CT system is detected, and images of bones are removed from the field encircled with the delineation of the body surface. The delineations of blood vessels are detected in the tomographic image having the bone images removed therefrom. The tomographic image having the bone images removed therefrom is used to score calcium. Only the intravascular calcium scores obtained using the fields inside the delineations of the blood vessels are displayed.

Further objects and advantages of the present invention will be apparent from the following description of the preferred embodiments of the invention as illustrated in the accompanying drawings.

BRIEF DESCRIPTION OF THE DRAWINGS

FIG. 6 is a schematic view showing a tomographic image that has bone images removed therefrom.

FIG. 7 is a schematic view showing a tomographic image that has the delineations of blood vessels detected therein.

FIG. 8 lists ranks of CT numbers.

FIG. 9 is a schematic view showing a tomographic image that has calcium scores superposed thereon.

DETAILED DESCRIPTION OF THE INVENTION

Figure 1:
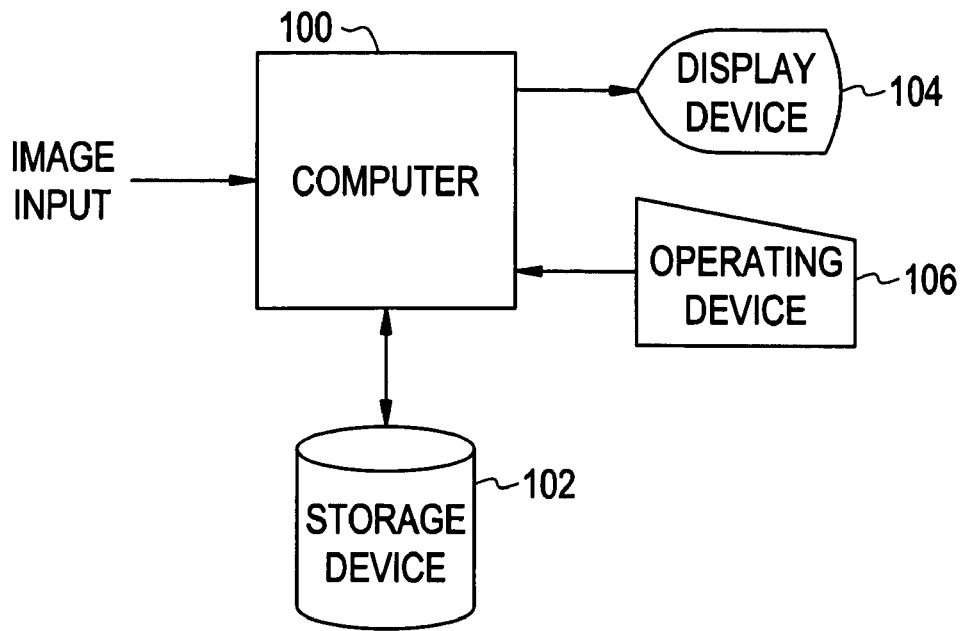
FIG. 1 is a block diagram of a calcium scoring system.

The best mode for implementing the present invention will be described with reference to drawings below. Noted is that the present invention is not limited to the best mode for implementing the present invention. FIG. 1 is a block diagram showing a calcium scoring system. The calcium scoring system is an example of the best mode for implementing the present invention. The configuration of the present system provides an example of the best mode for implementing the present invention in a calcium scoring system. Actions to be performed in the present system provide an example of the best mode for implementing the present invention in a calcium scoring method.

As shown in FIG. 1, the present system includes a computer 100. The computer 100 receives an image to be used to score calcium. The computer 100 includes a storage device 102. The received image is stored in the storage device 102. Moreover, various kinds of data and programs that are used by the computer are stored in the storage device 102. The computer 100 runs the programs stored in the storage device 102, whereby various data handling processes relevant to calcium scoring are executed.

Moreover, the computer 100 includes a display device 104 and an operating device 106. An image and other information sent from the computer 100 are displayed on the display device 104. A user manipulates the operating device 106, whereby various instructions or pieces of information are transmitted to the computer 100. The user can use the display device 104 and operating device 106 to interactively operate the present system.

Figure 2:
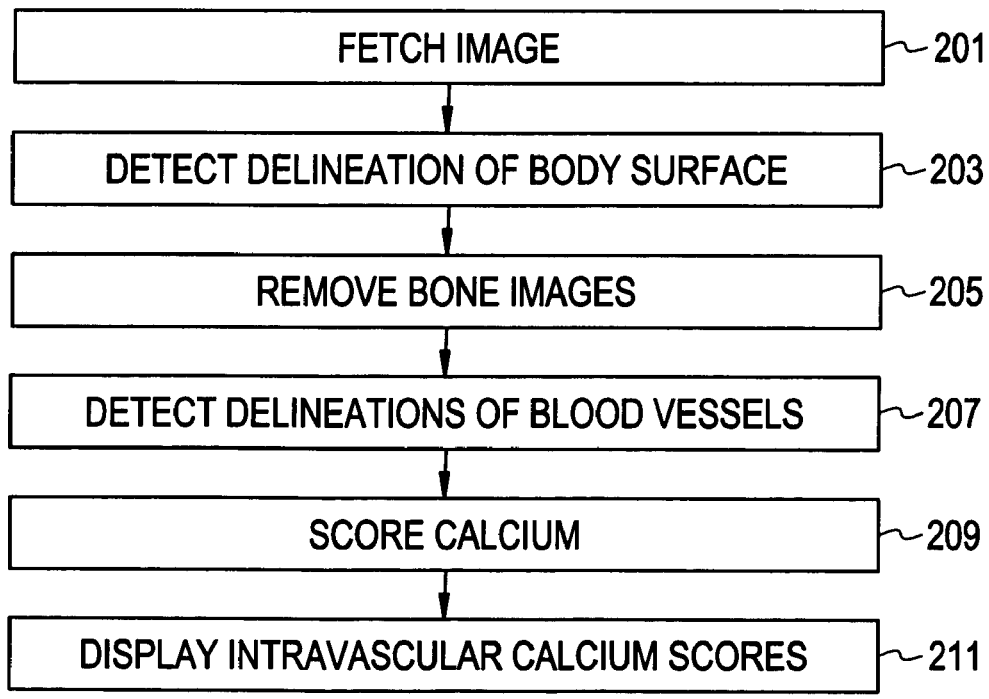
FIG. 2 is a flowchart describing calcium scoring.

Actions to be performed in the present system will be described. FIG. 2 is a flowchart describing the actions to be performed in the present system. The actions to be performed in the present system are carried out when the computer 100 runs the programs stored in the storage device 102.

Figure 3:
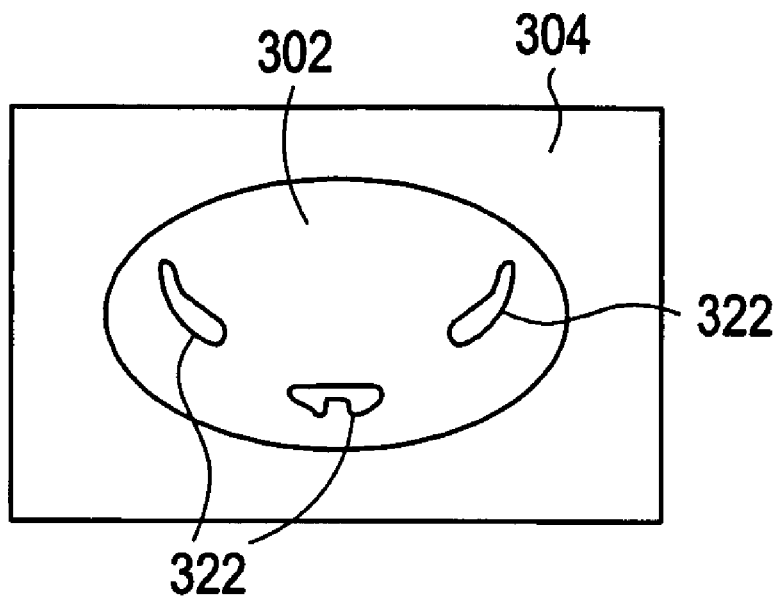
FIG. 3 is a schematic view showing a tomographic image.

As described in the drawing, an image is fetched in stage 201. Consequently, for example, an image like the one shown in FIG. 3 is stored in the storage device 102. The image is, for example, a tomographic image produced by an X-ray CT system and a half-tone image. FIG. 3 schematically shows the image. The image includes an image of a parenchyma 302 and a background 304. The parenchyma image 302 contains images of bones 322. Incidentally, images of tissues other than the bones are also contained but are not illustrated.

In stage 203, the delineation of a body surface is detected. The computer 100 detects the delineation of the body surface. The computer 100 is an example of a body surface delineation detecting means included in the present invention. The delineation of the body surface corresponds to the contour of the parenchyma image 302.

In order to detect the contour of the parenchyma image 302, first, the image is binary-coded. The binary coding is performed using an appropriate threshold. A value permitting distinction of the parenchyma image 302 from the background 304 is adopted as the threshold.

The threshold is obtained from, for example, a histogram indicating pixel values. The histogram of pixel values falls into a histogram indicating a group of values of pixels constituting the parenchyma image 302 and a histogram indicating a group of values of pixels constituting the background 304. Therefore, a threshold distinguishing one histogram from the other can be readily obtained.

Through binary coding, the parenchyma image 302 is represented by pixel values of "1", and the background 304 is represented by pixel values of "0". The Seed Fill algorithm is applied to the binary-coded images. Consequently, the inside of the border between the parenchyma image 302 and background 304 is filled with pixels having the same value.

Figure 4:
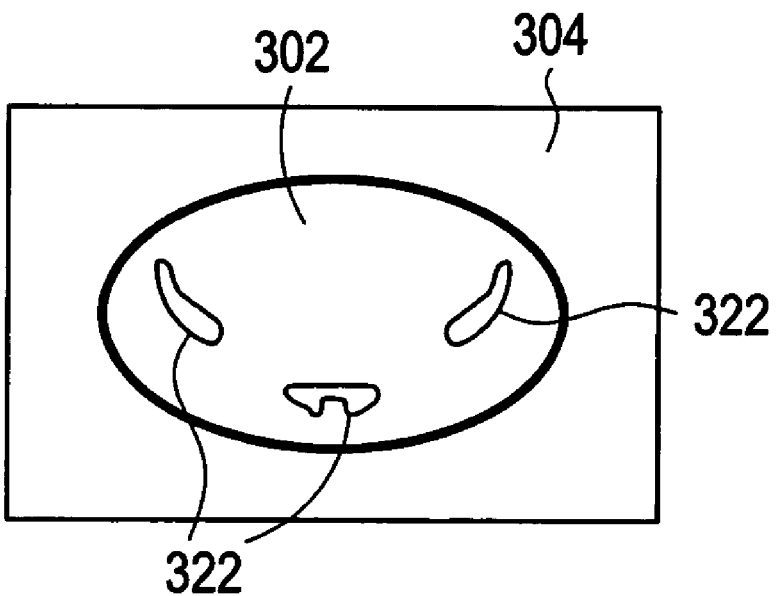
FIG. 4 is a schematic view showing a tomographic image that has the delineation of a body surface detected therein.

A 3×3 mask is applied to the pixels constituting the processed image. The center pixel of each matrix of 3 pixels in rows and columns is checked to see if the value of the center pixel is larger than the other pixels adjoining it in eight directions. If the value of the center pixel is larger, the center pixel is regarded as a pixel contained in the contour. Consequently, as indicated with a bold line in FIG. 4, the contour of the parenchyma image 302 is detected. After a tomographic image is binary-coded, the lineation of a body surface is detected. The lineation of the body surface can therefore be detected appropriately.

Next, in stage 205, the bone images are removed. The computer 100 removes the bone images. The computer 100 is an example of a bone image removing means included in the present invention. The bone images are removed based on CT numbers. The pixels constituting the bone images 322 assume higher CT numbers than the pixels constituting the images of the other tissues. For this reason, the bone images can be discriminated and removed from the parenchyma image 302. For the removal of the bone images 322, preferably, the pixel values representing the images other than the images of the bones are made uniform so that the bone images 322 can be correctly discriminated.

Figure 5:
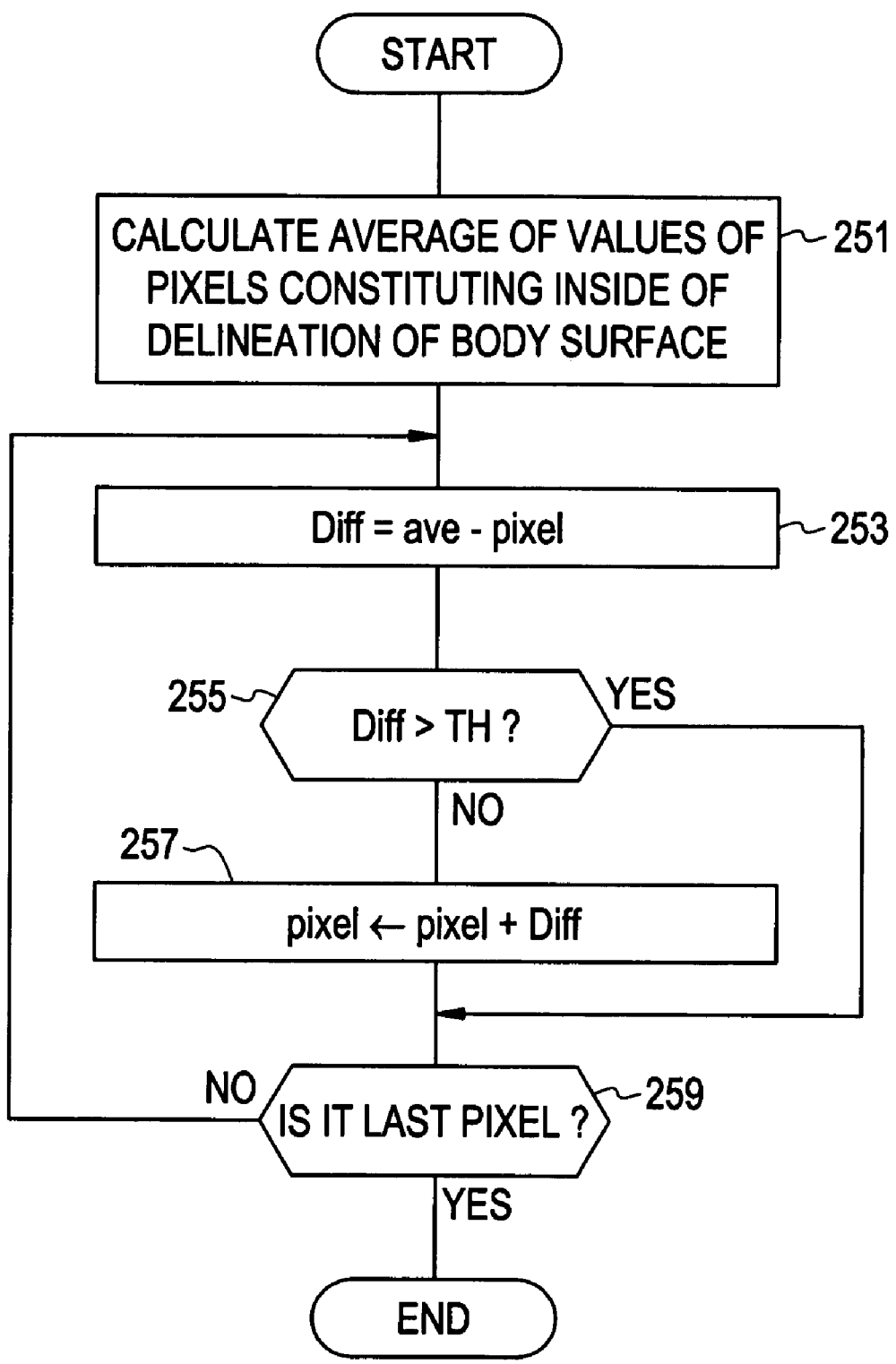
FIG. 5 is a flowchart describing part of calcium scoring.

According to a procedure like the one described in FIG. 5, the pixel values representing the images other than the images of the bones are made uniform. As described, at step 251, an average ave of the values of the pixels inside the delineation of the body surface is calculated. The pixels whose values are averaged include four pixels inside the right-hand part of the delineation of the body surface corresponding to the contour of the parenchyma image 302, and four pixels inside the left-hand part thereof.

Thereafter, at step 253, the following calculation is performed:

$$\text{Diff}=\text{ave}-\text{pixel} \quad (1)$$

where pixel denotes the value of one pixel contained in the image. The calculation provides the difference Diff of a pixel value from the average ave.

Thereafter, at step 255, the difference Diff is checked to see if it is larger than a predetermined threshold TH. The threshold TH is determined based on the difference of the CT number relevant to the bones from the average CT number relevant to the other tissues.

If the difference Diff is larger than the predetermined threshold TH, the pixel value is left intact. Otherwise, the difference is added to the pixel value at step 257, and the resultant value is adopted as a new pixel value. Consequently, the pixel value is converted into the average ave. Eventually, the pixel values representing the bone images 322 are left intact but the pixel values representing the images of the tissues other than the bones are converted into the average ave.

Thereafter, at step 259, the pixel having undergone the foregoing processing is checked to see if it is the last pixel contained in the image. If the pixel is not the last pixel, control is returned to step 253. The same processing as the aforesaid one is performed on a new pixel. The processing is repeated for all pixels constituting the image. Consequently, the pixel values representing the bone images 322 are left intact, but the pixel values representing the images of the tissues other than the bones are uniformly converted into the average ave. This processing may be called calibration.

In the calibrated image, the difference between the histogram indicating the group of pixel values representing the images of bones and the histogram indicating the group of pixel values representing the images of tissues other than the bones become more outstanding. A threshold used to discriminate the bone images is obtained from a histogram indicating pixel values representing the calibrated image. As mentioned above, after pixel values representing the images of tissues other than the bones are made uniform, the bone images are removed. Consequently, the bone images can be removed appropriately.

The threshold is used to discriminate the bone images 322, whereby the bone images 322 are removed from the tomographic image. In order to remove the bone images 322, for example, the pixel values representing the bone images are set to 0s. This results in an image having the bone images 322, as shown in FIG. 6, removed therefrom (the luminance values of the bone images 322 lowered).

In stage 207, the delineations of blood vessels are detected in the image having the bone images removed therefrom. The computer 100 detects the delineations of the blood vessels.

The computer 100 is an example of a blood vessel delineation detecting means. In order to detect the delineations of the blood vessels, for example, the Canny edge detector is employed. The Canny edge detector detects, for example, as shown in FIG. 7, the delineations of the blood vessels 324. In addition to the delineations of the blood vessels, the contours of images of other tissues are detected. However, the contours of the images of other tissues are not shown.

The Canny edge detector is optimal for detection of the delineations of blood vessels because it has a superior capability to detect edges, that is, the contours of images. However, the present invention is not limited to the Canny edge detector, but any other edge detector may be adopted.

Thereafter, at step 209, calcium is scored. The computer 100 scores calcium. The computer 100 is an example of a scoring means included in the present invention. Calcium is scored according to, for example, the Agatston and Janowitz scoring method. The score is expressed with a product of a rank of a CT number calculated from a pixel value by the size of a field composed of successive pixels whose CT numbers rank the same. The Agaston and Janowitz scoring method is preferred because of the high clinical value. Nevertheless, the present invention is not limited to the Agatston and Janowitz scoring method, but the volume scoring or any other appropriate calcium scoring method may be adopted.

Calcium is stored using the tomographic image having the bone images removed therefrom. This means that calcium contained in the bones is not scored. Consequently, scoring calcium can be achieved efficiently.

FIG. 8 lists the association of CT numbers with ranks. As shown in the drawing, CT numbers 130 to 199 rank first. CT numbers 200 to 299 rank second. CT numbers 300 to 399 rank third. CT numbers 400 or more ranks fourth.

Thereafter, at step 211, the intravascular calcium scores are displayed. The calcium scores are displayed on the display device 104 by the computer 100. The computer 100 and display device 104 serve as an example of a display means included in the present invention. Displayed as the intravascular calcium scores are not all of the calcium scores obtained at step 209 but only the calcium scores obtained from the insides of the delineations of the blood vessels.

Scoring calcium at step 209 is performed all over the image. If any tissue other than the blood vessels has a calcified part, the calcium score of the part is obtained. However, the calcium scores to be displayed are limited to the intravascular calcium scores. The calcium score of the calcified part of any other tissue is therefore not displayed. Consequently, the intravascular calcium scores 326 alone are displayed as shown in FIG. 9.

Scoring calcium at step 209 may be performed using the insides of the delineations of the blood vessels alone. Thus, only the intravascular calcium scores 326 may be displayed.

The calcium scores 326 are displayed in such a manner that a calcium score is classified into any of, for example, three levels of high, middle, and low levels, and then displayed as hues or a color scale associated with the classified level. The color scales associated with the high, middle, and low levels of calcium scores are graduated with hues of red, yellow, or blue. However, the color scales are not limited to the foregoing ones but may be graduated with any other color hues. Moreover, the number of levels is not limited to three but may be 256 or zero.

Since calcium scores are displayed as mentioned above, intravascular calcium scores may be intuitively grasped at sight. Namely, clinically significant information such as calcium deposited on an intravascular wall can be readily acquired.

Many widely different embodiments of the invention may be configured without departing from the spirit and the scope of the present invention. It should be understood that the present invention is not limited to the specific embodiments described in the specification, except as defined in the appended claims.

The invention claimed is:

1. A calcium scoring method comprising the steps of:
   detecting the delineation of a body surface in a tomographic image produced by an X-ray CT system, after the tomographic image is binary-coded;
   removing images of bones from a field encircled with the delineation of the body surface;
   detecting delineations of blood vessels in the tomographic image having the bone images removed therefrom;
   scoring calcium using the tomographic image having the bone images removed therefrom; and
   displaying only intravascular calcium scores obtained using fields inside the delineations of the blood vessels.

2. A calcium scoring method according to claim 1, wherein the bone images are removed after values of pixels constituting images of tissues other than the bones are made uniform.

3. A calcium scoring method according to claim 1, wherein the delineations of blood vessels are detected using a Canny edge detector.

4. A calcium scoring method according to claim 1, wherein calcium is scored according to the Agatston and Janowitz scoring method.

5. A calcium scoring method according to claim 1, wherein the calcium scores are displayed in a form of color scales.

6. A calcium scoring system comprising:
   a body surface delineation detecting device for detecting delineation of a body surface in a tomographic image produced by an X-ray CT system, wherein the delineation of the body surface is detected after the tomographic image is binary-coded;
   a bone image removing device for removing images of bones from a field encircled with the delineation of the body surface;
   a blood vessel delineation detecting device for detecting delineations of blood vessels in the tomographic image having the bone images removed therefrom;
   a scoring device for scoring calcium using the tomographic image that has the bone images removed therefrom; and
   a display device for displaying only intravascular calcium scores obtained using fields inside the delineations of the blood vessels.

7. A calcium scoring system according to claim 6, wherein the bone images are removed after values of pixels constituting images of tissues other than the bones are made uniform.

8. A calcium scoring system according to claim 6, wherein the delineations of blood vessels are detected using a Canny edge detector.

9. A calcium scoring system according to claim 6, wherein calcium is scored according to the Agatston and Janowitz scoring method.

10. A calcium scoring system according to claim 6, wherein the calcium scores are displayed in a form of color scales.

11. A calcium scoring method comprising:
    acquiring a computed tomography (CT) image of a portion of a body, the CT image including a background, organ tissue, and a bone;
    detecting a border contour of the organ tissue in the acquired image;

removing the bone from the acquired image to generate a boneless image, said removing based on CT numbers within the acquired image;

detecting delineations of blood vessels within the organ tissue in the boneless image, after the boneless image is binary-coded; and scoring calcium within at least the detected blood vessel delineations in the boneless image.

12. A method in accordance with claim 11 wherein said detecting a border contour further comprises:

generating a binary image of pixels that are representative of the background and the organ tissue;

filling the binary image such that pixels within a border between the organ tissue and the background each have a common value; and applying a mask to the filled binary image to determine border pixels, the border pixels forming the border contour.

13. A method in accordance with claim 11 wherein said removing the bone further comprises:

making pixels with the background and pixels within the organ tissue uniform; and applying a first threshold to the uniform pixels and pixels within the bone to remove the pixels within the bone from the acquired image.

14. A method in accordance with claim 13 wherein said making pixels with the background and pixels within the organ tissue uniform further comprises:

calculating an average value of pixels within an area inside the border contour;

subtracting a pixel value of each of the pixels within the area from the calculated average value to determine a difference value; and comparing the difference value of each of the pixels within the area to a second threshold to determine a calibrated value of each of the pixels within the area.

15. A method in accordance with claim 14 further comprising:

if the difference value of a pixel is greater than the second threshold, setting the calibrated value of the pixel to the pixel value of the pixel; and if the difference value of the pixel is less than or equal to the second threshold, setting the calibrated value of the pixel to be equal to the pixel value of the pixel plus the difference value of the pixel to make uniform the calibrated values of pixels having a difference value not greater than the second threshold.

16. A method in accordance with claim 11 wherein said scoring calcium further comprises:

scoring calcium within the boneless image; and displaying a calcium score for pixels within the detected blood vessel delineations.

17. A method in accordance with claim 11 further comprising:

classifying the calcium score as one classification of a plurality of predetermined classifications, wherein each classification of the plurality of classifications corresponds with one color of a plurality of predetermined colors; and displaying the calcium score in the one color that corresponds to the one classification of the plurality of predetermined classifications.

18. A method in accordance with claim 11 wherein said scoring calcium further comprises expressing a calcium score as a product of a rank of a CT number, which is calculated from each pixel value, and a size of a field of pixels with the rank.

* * * * *